United States Patent
Kawanaka

(10) Patent No.: US 9,254,345 B2
(45) Date of Patent: Feb. 9, 2016

(54) MOISTURE-ABSORBING AND DEODORIZING FIBER, METHOD FOR MANUFACTURING THE SAME, AND FIBER STRUCTURE CONTAINING THE SAME

(71) Applicant: JAPAN EXLAN COMPANY LIMITED, Osaka (JP)

(72) Inventor: Naoki Kawanaka, Okayama (JP)

(73) Assignee: JAPAN EXLAN COMPANY LIMITED, Osaka (JP)

( * ) Notice: Subject to any disclaimer, the term of this patent is extended or adjusted under 35 U.S.C. 154(b) by 51 days.

(21) Appl. No.: 14/356,435

(22) PCT Filed: Nov. 7, 2012

(86) PCT No.: PCT/JP2012/078785
§ 371 (c)(1),
(2) Date: May 6, 2014

(87) PCT Pub. No.: WO2013/069659
PCT Pub. Date: May 16, 2013

(65) Prior Publication Data
US 2014/0314828 A1 Oct. 23, 2014

(30) Foreign Application Priority Data

Nov. 10, 2011 (JP) ................................. 2011-246113

(51) Int. Cl.
| | | |
|---|---|---|
| *A61L 9/01* | (2006.01) | |
| *A61K 9/70* | (2006.01) | |
| *C08F 8/30* | (2006.01) | |
| *A61L 15/46* | (2006.01) | |
| *B01D 53/02* | (2006.01) | |
| *D06M 15/356* | (2006.01) | |
| *B01J 20/28* | (2006.01) | |
| *B01J 20/32* | (2006.01) | |

(52) U.S. Cl.
CPC ................. *A61L 15/46* (2013.01); *B01D 53/02* (2013.01); *B01J 20/28023* (2013.01); *B01J 20/3208* (2013.01); *B01J 20/3272* (2013.01); *B01J 20/3293* (2013.01); *D06M 15/356* (2013.01); *A61L 9/01* (2013.01); *B01D 2253/202* (2013.01); *B01D 2257/80* (2013.01); *B01D 2257/90* (2013.01)

(58) Field of Classification Search
None
See application file for complete search history.

(56) References Cited

U.S. PATENT DOCUMENTS

| | | | | |
|---|---|---|---|---|
| 5,292,822 A | * | 3/1994 | Tanaka | C08F 8/30 525/329.1 |
| 5,897,673 A | * | 4/1999 | Nishida | D01F 1/10 424/76.1 |
| 2006/0153903 A1 | * | 7/2006 | Ieno | A61K 8/44 424/443 |

FOREIGN PATENT DOCUMENTS

| | | |
|---|---|---|
| EP | 0 889 158 | 1/1999 |
| JP | 3-218766 | 9/1991 |
| JP | 9-31853 | 2/1997 |
| JP | 9-241928 | 9/1997 |
| JP | 10-245778 | 9/1998 |
| JP | 2000-080569 | 3/2000 |
| JP | 2009-7728 | 1/2009 |
| JP | 2010-216051 | 9/2010 |

OTHER PUBLICATIONS

Machine translation for JP 3-218766; published as JP 2849426 B; downloaded Aug. 20, 2015.*
Supplementary European Search Report dated Jun. 16, 2015 in European Application No. EP 12 84 7650.
International Search Report issued Jan. 22, 2013 in International (PCT) Application No. PCT/JP2012/078785.

* cited by examiner

*Primary Examiner* — Jeffrey T Palenik
(74) *Attorney, Agent, or Firm* — Wenderoth, Lind & Ponack LLP

(57) ABSTRACT

In the prior art, there has not been provided a fiber that can quickly and persistently deodorize and absorb the smell and the damp feeling due to body fluid generated from the body. The present invention provides a fiber having such property, and specifically provides a moisture-absorbing and deodorizing fiber, characterized in that, a basic polymer is ionically-bonded in an amount of 0.2 to 4 mmol/g as an amount of amino group onto the surface of a moisture-absorbing fiber having a crosslinked structure and also having 3 to 8 mmol/g of carboxyl group.

7 Claims, No Drawings

__US 9,254,345 B2__

MOISTURE-ABSORBING AND DEODORIZING FIBER, METHOD FOR MANUFACTURING THE SAME, AND FIBER STRUCTURE CONTAINING THE SAME

TECHNICAL FIELD OF THE INVENTION

The present invention relates to a moisture-absorbing and deodorizing fiber having both moisture-absorbing performance and deodorizing performance or, particularly, an excellent deodorizing performance to the smell of sweat and the smell of aged persons as well.

BACKGROUND ART

As a result of changes in our living environment in recent years, consciousness to smell and damp feeling has increased and there has been a demand for quickly and persistently solving the smell and the damp feeling due to body fluid generated from the body. With regard to the smell for example, consciousness for the smell of aged persons and the smell of sweat is high. The smell of sweat is mostly constituted from ammonia, acetic acid and isovaleric acid, and the smell of aged persons is constituted from nonenal in addition to ammonia, acetic acid and isovaleric acid. A deodorizing method is roughly classified into physical deodorization, chemical deodorization, sensory deodorization (masking), etc. Activated charcoal which is very excellent as a physical deodorizer has problems such as that preparing it into fine particles is difficult and that fixation onto the fiber is difficult making the color of the fiber bad. Further, in a physical deodorization, the performance is significantly deteriorated due to an operation such as washing. Furthermore, in a deodorant utilizing a catalytic action, its fast-acting effect is low. In the deodorization using perfume or the like, its use is limited since the perfume itself may become a bad smell depending on the preference of a person and also the olfactory fatigue is resulted. As a method which can overcome the above problems and is still excellent in the fast-acting effect and the persisting performance, there is a method using a chemical neutralization method.

For example, the patent document 1 discloses a basic substance-deodorizing fiber due to an H-form carboxyl group and the patent document 2 discloses an acidic substance-deodorizing fiber due to a primary amino group. However, in the deodorizing methods using a chemical neutralization reaction of the prior art as such, it is necessary that, for achieving the deodorizing performance to any of an acidic substance and a basic substance as the smell components, deodorization for one of the components had to be neglected. Thus, such deodorizing methods are not effective for the complex smell such as the smell of sweat and the smell of aged persons.

In addition, although the deodorizing fiber having both acidic group and basic group being disclosed in the patent document 3 has deodorizing performance to both of the basic and the acidic substances, the deodorizing component is present only on the fiber surface whereby there are both problem that the deodorizing performance is insufficient and that the moisture-absorbing performance to damp feeling is insufficient.

PRIOR ART DOCUMENTS

Patent Documents

Patent Document 1: Japanese Patent Application Laid-Open (JP-A) No. 245778/98
Patent Document 2: Japanese Patent Application Laid-Open (JP-A) No. 241928/97
Patent Document 3: Japanese Patent Application Laid-Open (JP-A) No. 2000-80569

DISCLOSURE OF THE INVENTION

Problem that the Invention is to Solve

An object of the present invention is to provide, in the field of clothing and bedding, a moisture-absorbing and deodorizing fiber which have both of the high deodorizing performance to the complex smell such as smell of sweat and smell of aged persons and the moisture-absorbing performance reducing the damp feeling and, in addition, which can keep an excellent deodorizing performance even upon repeated washings. Such fiber has not been provided in the prior art.

Means for Solving the Problem

The above object of the present invention is achieved by the following means:

(1) A moisture-absorbing and deodorizing fiber, characterized in that, a basic polymer is ionically-bonded in an amount of 0.2 to 4 mmol/g as an amount of amino group onto the surface of a moisture-absorbing fiber having a crosslinked structure and also having 3 to 8 mmol/g of carboxyl group.

(2) The moisture-absorbing and deodorizing fiber according to (1), wherein moisture-absorbing rate under the condition of 20° C. and 65% RH is 20 to 60% by weight.

(3) The moisture-absorbing and deodorizing fiber according to (1) or (2), wherein ammonia-removing rate is 70% or more, acetic acid-removing rate is 80% or more, isovaleric acid-removing rate is 85% or more and nonenal-removing rate is 75% or more.

(4) The moisture-absorbing and deodorizing fiber according to any of (1) to (3), wherein retention rate of the deodorizing performance to each of ammonia, acetic acid, isovaleric acid and nonenal after washing for ten times is 90% or more.

(5) The moisture-absorbing and deodorizing fiber according to any of (1) to (4), wherein average molecular weight of the basic polymer is 300 or more.

(6) A method for manufacturing the moisture-absorbing and deodorizing fiber mentioned in any of (1) to (5), characterized in that, a basic polymer is conically-bonded to a moisture-absorbing fiber in which the ratio of salt-form carboxyl group to H-form carboxyl group is within a range of 40:60 to 100:0.

(7) A moisture-absorbing and deodorizing fiber structure containing the moisture-absorbing and deodorizing fiber mentioned in any of (1) to (5).

Advantages of the Invention

The moisture-absorbing and deodorizing fiber of the present invention can achieve not only high moisture-absorbing performance which reduces the damp feeling caused by body fluid generated from the body so as to actualize the comfortable humidity environment, but also fast-acting and persisting deodorizing performance to the complex smell such as smell of sweat and smell of aged persons.

BEST MODE FOR CARRYING OUT THE INVENTION

It is necessary that the moisture-absorbing fiber adopted in the present invention has a crosslinked structure and also having carboxyl group. Examples of the moisture-absorbing fiber as such include a polyacrylate-based crosslinked fiber, a maleic anhydride-based crosslinked fiber, an alginate-based crosslinked fiber, etc. in which a monomer containing a hydrophilic group such as carboxyl group or an alkali metal base thereof is copolymerized with a monomer containing a hydroxyl group which can form an ester crosslinked structure as a result of reaction with carboxyl group followed by introducing an ester crosslinked bond thereinto; and an acrylate-based crosslinked fiber, etc. in which crosslinked structure is introduced into acrylonitrile-based fiber using a crosslinking agent followed by hydrolyzing so as to introduce the carboxyl group thereinto. An acrylate-based crosslinked fiber is particularly preferred as a moisture-absorbing fiber to be adopted in the present invention since it is possible to obtain a fiber having excellent moisture-absorbing property as a result of controlling a crosslinking condition using a crosslinking agent and a hydrolyzing condition. Hereinafter, the moisture-absorbing and deodorizing fiber of the present invention will be illustrated in detail by taking such an acrylate-based crosslinked fiber as an example.

An acrylonitrile-based fiber which is a material fiber for the acrylate-based crosslinked fiber is manufactured by a known method starting from an acrylonitrile-based polymer. As to the composition of the polymer, it is preferred that acrylonitrile is 40% by weight or more. Acrylonitrile is more preferred to be 50% by weight or more, and further preferred to be 80% by weight or more. As will be mentioned later, a crosslinked structure is introduced into the fiber by the reaction of a nitrile group in the acrylonitrile-based copolymer forming the acrylonitrile-based fiber with a nitrogen-containing compound such as a hydrazine-based compound. The crosslinked structure greatly affects the physical properties of the fiber. When the copolymerizing composition of acrylonitrile is too small, the crosslinked structure is inevitably small whereupon there is a possibility that the physical properties of the fiber become insufficient. When the copolymerizing composition is made within the above range, a good result is apt to be achieved.

With regard to a copolymerizing component other than acrylonitrile in the acrylonitrile-based polymer, there is no particular limitation so far as it is a monomer copolymerizable with acrylonitrile. Specific examples thereof include a monomer containing a sulfonic acid such as methallyl sulfonic acid or p-styrenesulfonic acid and a salt thereof; a monomer containing a carboxylic acid such as (meth)acrylic acid or itaconic acid and a salt thereof; and a monomer such as styrene, vinyl acetate, (meth)acrylate or (meth)acrylamide; etc.

As to the form of the acrylonitrile-based fiber adopted in the present invention, any of the forms of staple, tow, yarn, knitted/woven thing, non-woven fabric, etc. is acceptable. It is also possible to adopt an intermediate product during the manufacturing steps, waste fiber, etc.

With regard to a crosslinking agent for introducing a crosslinked structure into an acrylonitrile-based fiber, although any of the known crosslinking agents may be used, it is preferred to use a nitrogen-containing compound in view of efficiency of the crosslinking reaction and of easiness in the handling. It is necessary that the nitrogen-containing compound has two or more nitrogen atoms in a molecule. No crosslinking reaction takes place when nitrogen atom numbers in a molecule are less than two. As to the specific examples of the nitrogen-containing compound, although there is no particular limitation therefor so far as formation of the crosslinked structure is possible, an amino compound and a hydrazine compound having two or more primary amino groups are preferred. Examples of the amino compound having two or more primary amino groups include a diamine compound such as ethylenediamine or hexamethylenediamine; a triamine compound such as diethylenetriamine, 3,3'-iminobis(propylamine) or N-methyl-3,3'-iminobis(propylamine); a tetramine compound such as triethylenetetramine, N,N'-bis(3-aminopropyl)-1,3-propylenediamine or N,N'-bis(3-aminopropyl)-1,4-butylene-diamine; and a polyamine compound such as polyvinylamine or polyallylamine having two or more primary amino groups. As to the hydrazine compound, there may be exemplified hydrazine hydrate, hydrazine sulfate, hydrazine hydrochloride, hydrazine hydrobromide and hydrazine carbonate. Although there is no particular limitation for the upper limit of nitrogen atom numbers in a molecule, it is preferred to be 12 or smaller, more preferred to be 6 or smaller, and further preferred to be 4 or smaller. When the nitrogen atom numbers in a molecule exceed the above upper limit, the crosslinking agent molecule becomes too big and there may be a case wherein the crosslinkage is hardly introduced into the fiber.

With regard to the condition for introducing the crosslinked structure, there is no particular limitation therefor but it can be appropriately selected by taking the reactivity of the adopted crosslinking agent with an acrylonitrile-based fiber, amount of crosslinked structure, moisture-absorbing rate, difference in saturated moisture-absorbing rates, physical properties of the fiber, etc. into consideration. When, for example, a hydrazine compound is used as a crosslinking agent, there is exemplified a method wherein the above-mentioned acrylonitrile-based fiber is dipped in an aqueous solution prepared by addition of the above-mentioned hydrazine compound so as to make the hydrazine concentration 3 to 40% by weight followed by treating at 50 to 120° C. within 5 hours.

The fiber into which the crosslinked structure is introduced is subjected to a hydrolyzing treatment using an alkaline metal compound. As a result of such a treatment, nitrile group and amide group existing in the fiber are hydrolyzed to form carboxyl group. The carboxyl group is a factor for achieving the characteristic properties such as moisture-absorbing/desorbing property, exothermic property upon moisture absorption, deodorizing property or ionic bonding property to a basic polymer which will be mentioned later in the acrylate-based crosslinked fiber. Generally, it is desirable to form preferably 3 to 8 mmol/g and more preferably 5 to 8 mmol/g of carboxyl group in terms of the total carboxyl group amount. The amount of the formed carboxyl group can be adjusted by means of the hydrolyzing treatment condition.

In the carboxyl group used here, there are a salt-form carboxyl group, a counter-ion of which is a cation except hydrogen ion and also an H-form carboxyl group, a counter-ion of which is hydrogen ion. Although their ratio can be freely adjusted, it is desirable to adjust the ratio of the salt-form carboxylic group to the H-form carboxyl group within a range of preferably 40:60 to 100:0, more preferably 40:60 to 90:10, and further preferably 40:60 to 80:20. It is preferred to adjust to the above ratio because the salt-form carboxyl group can be ionically-bonded to a basic polymer under milder conditions and the H-form carboxyl group is a functional group having acidity and is a site for adsorb and deodorize the ammonia commonly existing in both of the smell of sweat and the smell of aged persons. Incidentally, even when the ratio of the H-form carboxyl group is 0, ammonia and the like can be deodorized to some extent by being dissolved in water absorbed with the fiber.

As to the type of the metal constituting the salt-form carboxyl group, one or more member(s) may be selected depending upon the necessary characteristic property from alkali metal such as lithium, sodium or potassium, alkali earth metal such as magnesium or calcium and other metal such as manganese, copper, zinc or silver. Particularly when polyvalent metal ion such as magnesium or calcium is adopted, there is the tendency that much basic polymer is adhered and that is advantageous.

With regard to a method for adjusting the ratio of the salt-form carboxyl group to the H-form carboxyl group to the above-mentioned range, examples thereof include a method of conducting an ion-exchange treatment using metal salt such as nitrate, sulfate or hydrochloride, a method of conducting an acid treatment using nitric acid, sulfuric acid, hydrochloric acid or formic acid and a method of conducting a pH adjusting treatment using an alkaline metal compound or the like.

The acrylate-based crosslinked fiber prepared as such is then subjected to a treatment for adhering a basic polymer onto the fiber surface. The basic polymer as such is preferred to be soluble in water and examples thereof include polyethyleneimine and polyvinylpyrrolidone.

Polyethyleneimine is particularly advantageous since an amino group density in the polymer is as high as 18 to 21 mmol/g and its deodorizing performance to acidic substance such as acetic acid or isovaleric acid and to aldehyde such as nonenal is high. An example of the treating condition is that a fiber is dipped in an aqueous solution having the basic polymer concentration of 0.2 to 10% by weight and preferably 0.2 to 3% by weight, and treated at 20 to 80° C. for 10 to 120 minutes. As to the adhering amount of the basic polymer, it is necessary to adhere in such a manner that the adhered amount of amino group to the fiber is made 0.2 to 4 mmol/g.

When an acrylate-based crosslinked fiber is dipped in an aqueous solution of basic polymer, an amino group of the basic polymer forms ionic bonding to a carboxyl group of the acrylate-based crosslinked fiber but, since the molecular size of the basic polymer is big, the basic polymer is not permeated into the inner area of the fiber but remains on the surface. Accordingly, it is likely that the fiber after dipping is in a two-layer structure wherein free amino acid expressing the deodorizing performance to acidic substance and aldehyde is present on the surface of the fiber while, in the inner area of the fiber, H-form carboxyl group expressing the deodorizing performance to basic substance is present. In addition, as a result of the treatment with an aqueous solution, many ionic bondings are apt to be formed. Since the basic polymer is adhered on the fiber surface due to such polyionic bondings, it is likely that, even by washing, the basic polymer is hardly detached and the deodorizing performance is maintained. On the contrary, when molecular weight of the basic polymer is low, the molecule is apt to be evaporated whereupon, even if it is once adhered on the fiber surface, there is a risk that it is detached from the fiber to generate an amine smell. Accordingly, as to a basic polymer, that which is soluble in water and has high molecular weight as mentioned above is preferred and, as to the number-average molecular weight, that of 300 to 70,000 is advantageous.

Here, with regard to the characteristic that the deodorizing performance is maintained even subjected to washing, etc., it is preferred in the moisture-absorbing and deodorizing fiber of the present invention in view of maintenance of the deodorizing performance to the smell of sweat and the smell of aged persons that the retention rate of deodorizing performance which will be mentioned later to each of ammonia, acetic acid, isovaleric acid and nonenal is 90% or more.

In the moisture-absorbing and deodorizing fiber of the present invention prepared as mentioned above, the adsorbing/deodorizing sites for an acidic substance and aldehyde are present on the surface layer of the fiber while the adsorbing/deodorizing for a basic substance and moisture-absorbing sites are present in the inner area of the fiber and, as a result, it is now possible that not only the comfortable humidity environment is actualized by reducing the damp feeling caused by body fluid generated from the body but also the fast-acting and persisting deodorizing performance to the complex smell such as the smell of sweat and the smell of aged persons is achieved.

The moisture-absorbing and deodorizing fiber of the present invention becomes more useful by forming a fiber structure either solely or by combining with other material. Examples of the external appearance shapes of such a fiber structure include wadding, yarn, knitted product, woven product, non-woven fabric, pile fabric, paper sheet-like one, etc. As to the embodiments how the moisture-absorbing and deodorizing fiber of the present invention is made to contained in the structure, there is such a one wherein the fiber is distributed therein substantially uniformly by means of mixing with other material and, in the case of a structure having plural layers, there are such ones wherein the moisture-absorbing and deodorizing fiber is made to exist by concentrating to any layer(s) (which may be either singular or plural), wherein the moisture-absorbing and deodorizing fiber is distributed in each layer in a specific ratio, etc.

In the fiber structure of the present invention, there are quite a lot of combinations of the forms of external appearance with the forms how the fiber is contained being exemplified above. What structure is to be prepared can be appropriately decided by taking the using manner of the final product (such as seasonal modification, kinesthetic modification, whether the product is underwear, interior ware or outer ware and the utilizing manner such as filter, curtain, carpet, bedclothes, cushion, insole, etc.), required function, how the moisture-absorbing and deodorizing fiber contributes in expressing the function, etc. into consideration.

There is no particular limitation for other materials which can be used together with the fiber structure of the present invention but the publicly used natural fibers, organic fibers, semi-synthetic fibers and synthetic fibers may be used. In addition, inorganic fibers, glass fibers, etc. may also be used depending upon the use. Specific examples thereof include cotton, linen, silk, wool, Nylon, rayon, polyester and acrylic fiber.

As to a method for manufacturing the fiber structure of the present invention, it is also possible to adopt a method wherein a fiber structure is manufactured using a moisture-absorbing fiber before adding a basic polymer and, after that, the fiber structure is treated with a basic polymer so that the moisture-absorbing and deodorizing fiber is formed in the fiber structure, in addition to a method wherein the fiber structure as mentioned above is manufactured using the previously-prepared moisture-absorbing and deodorizing fiber of the present invention. It is further possible to adopt a method wherein a moisture-absorbing fiber before adding a basic polymer thereto or a fiber structure using said fiber is dyed and then treated with a basic polymer.

EXAMPLES

The present invention will now be more specifically illustrated by way of the following Examples. The terms part (s) and percent (s) in Examples are those by weight unless otherwise mentioned. Amount of carboxyl group, amount of amino group, moisture-absorbing rate and smell-removing rate were determined according to the following methods:

(1) Amount of Carboxyl Group

A fiber sample (about 1 g) was dipped in 50 ml of a 1 mol/l aqueous hydrochloric acid solution for 30 minutes. After that, the fiber sample was dipped in water in a bath ratio of 1:500. After 15 minutes, drying was conducted when it was confirmed that the pH of the bath was 4 or higher. (In case the pH of the bath was lower than 4, washing with water was conducted again.) Then about 0.2 g of the well-dried fiber sample was precisely weighed (W1 [g]), 100 ml of water was added thereto and then 15 ml of a 0.1 mol/l aqueous sodium hydroxide solution, 0.4 g of sodium chloride and phenolphthalein were further added thereto followed by stirring. After 15 minutes, separation into the sample fiber and the filtrate was conducted by means of filtration and then the sample fiber was washed with water until coloration by phenolphthalein was no longer noted. The washing water and the filtrate at that time were combined and titrated with a 0.1 mol/l aqueous hydrochloric acid solution until coloration by phenolphthalein was no longer noted, to determine the consumed amount (V1 [ml]) of the aqueous hydrochloric acid solution. From the resulting measured value, amount of total carboxyl group was calculated according to the following formula:

$$\text{amount of carboxyl group [mmol/g]} = (0.1 \times 15 - 0.1 \times V1)/W1$$

(2) Ratio of Salt-Form Carboxyl Group to H-Form Carboxyl Group

Amount of the H-form carboxyl group was calculated by the same manner as in the above-mentioned method for measuring the amount of carboxyl group, except that the initial dipping into a 1 mol/l aqueous hydrochloric acid solution and the washing with water thereafter were not conducted. The resulting amount of the H-form carboxyl group was deducted from the above amount of the total carboxyl group to calculate the amount of the salt-form carboxyl group whereby the ratio of the salt-form carboxyl group to the H-form carboxyl group was determined.

(3) Amount of Amino Group

Let the amine value of the used basic polymer be A [mmol/g]. Weight of the fiber before treating with a basic polymer was measured and let it be B [g]. Weight of the fiber after treating with a basic polymer was measured and let it be C [g]. Amount of amino group was calculated according to the following formula:

$$\text{amount of amino group [mmol/g]} = A \times (C-B)/C$$

(4) Moisture-Absorbing Rate at 20° C. and 65% RH

A fiber sample (about 5.0 g) was dried at 105° C. for 16 hours in a hot-air drier to measure the weight (W2 [g]). Then the fiber sample was placed for 24 hours in a constant-temperature and constant-humidity container adjusted to 20° C. temperature and 65% RH. Weight of the fiber sample humidified as such was measured (W3 [g]). From the above measured results, moisture-absorbing rate at 20° C. and 65% RH (saturated moisture-absorbing rate) was calculated according to the following formula:

$$\text{moisture-absorbing rate at 20° C. and 65\% } RH[\%] = (W3-W2)/W2 \times 100$$

(5) Smell-Removing Rate

A fiber sample (0.5 g) was placed in a Tedlar bag and tightly closed and 1.5 l of air was infused thereinto. After that, the smell in a predetermined concentration (100 ppm for ammonia, 50 ppm for acetic acid, 40 ppm for isovaleric acid, 14 ppm for acetaldehyde or 14 ppm for nonenal) was infused into the Tedlar bag and, after being allowed to stand at room temperature for 120 minutes, concentration (W4) of the smell in the Tedlar bag was measured. With regard to the measurement, gas chromatography was used for isovaleric acid and nonenal while, for the smell of others, measurement was done using a Kitagawa gas detector tube. In addition, a blank to which no sample was added was also prepared in the same concentration and, after 120 minutes, concentration (W5) of the smell was measured to conduct a blank test. From the above result, smell-removing rate was calculated according to the following formula:

$$\text{smell-removing rate [\%]} = (W5-W4)/W5 \times 100$$

In accordance with the certification standards of the Japan Textile Evaluation Technology Council, it is certified that the fiber sample has a deodorizing effect for the smell of sweat when all requirements of 70% or more removing rate for ammonia, 80% or more removing rate for acetic acid and 85% or more removing rate for isovaleric acid are satisfied. It is also certified that the fiber sample has a deodorizing effect for the smell of aged persons when the requirement of 75% or more removing rate for nonenal is satisfied in addition to the above standards.

(6) Retention Rate of Deodorizing Performance

Retention rate of deodorizing performance is calculated by the following formula:

$$\text{Retention rate of deodorizing performance (\%)} = \{[\text{Smell-removing rate for fiber sample after washing for ten times}]/[\text{Smell-removing rate for fiber sample without washing}]\} \times 100$$

Incidentally, the washing is carried out in accordance with a method 103 (for washing machines of home use) of JIS L 0213.

Example 1

An acrylonitrile-based polymer comprising 90% of acrylonitrile and 10% of methyl acrylate was dissolved in a 48% aqueous sodium rhodanate solution to prepare a dope solution for spinning. This dope was subjected to spinning, washing with water, stretching, crimping and thermal treatment according to conventional methods to give a material fiber in 0.8 denier and 70 mm. To 1 kg of this material fiber was added 5 kg of 30% by weight of hydrazine hydrate followed by subjecting to a crosslinking treatment at 98° C. for 3 hours. An increased amount for nitrogen was 5.0%. The resulting crosslinked fiber was washed with water and 5 kg of 3% by weight of aqueous sodium hydroxide solution was added thereto followed by hydrolyzing at 90° C. for 1 hour. After that, treatment with a 1 mol/l aqueous nitric acid solution was conducted to transform the carboxyl group into an H-form and, after washing with water, pH was adjusted to 6.5 using a 1 mol/l aqueous sodium hydroxide solution. The amount of carboxyl group and the ratio of salt-form carboxyl group to H-form carboxyl group of the resulting acrylate-based crosslinked fiber are shown in Table 1. Then the fiber was dipped in a 2% aqueous solution of polyethyleneimine (number-average molecular weight: 600; amine value: 20 mmol/g) followed by treating at 50° C. for 60 minutes. After that, washing and drying treatments were carried out to give a moisture-absorbing and deodorizing fiber. The result of evaluation of the fiber is shown in Table 1.

Example 2

The same treatment as in Example 1 was carried out except that the hydrolyzing time was changed to 2 hours to give a moisture-absorbing and deodorizing fiber. The result of evaluation of the fiber is shown in Table 1.

Example 3

The same treatment as in Example 1 was carried out except that the hydrolyzing time was changed to 5 hours and polyethyleneimine was changed to polyethyleneimine having the number-average molecular weight of 70,000 (amine value: 18 mmol/g) to give a moisture-absorbing and deodorizing fiber. The result of evaluation of the fiber is shown in Table 1.

Example 4

The same treatment as in Example 2 was carried out except that the acrylate-based crosslinked fiber was dipped in a 1% aqueous solution of polyethyleneimine (number-average molecular weight: 10000; amine value: 18 mmol/g) to treat at 80° C. for 120 minutes followed by subjecting to washing with water and drying treatment to give a moisture-absorbing and deodorizing fiber. The result of evaluation of the fiber is shown in Table 1.

Example 5

The same treatment as in Example 4 was carried out except that the concentration of aqueous polyethyleneimine solution was changed to 2% to give a moisture-absorbing and deodorizing fiber. The result of evaluation of the fiber is shown in Table 1.

Example 6

The same treatment as in Example 4 was carried out except that polyethyleneimine was changed to polyethyleneimine having the number-average molecular weight of 1,800 (amine value: 19 mmol/g) to give a moisture-absorbing and deodorizing fiber. The result of evaluation of the fiber is shown in Table 1.

Example 7

The same treatment as in Example 4 was carried out except that an acrylate-based crosslinked fiber prepared, in a manufacturing process for obtaining the acrylate-based crosslinked fiber of Example 1, by changing the pH to be adjusted by a 1 mol/l aqueous sodium hydroxide solution to 4.2 was used in place of the acrylate-based crosslinked fiber of Example 2 to give a moisture-absorbing and deodorizing fiber. The result of evaluation of the fiber is shown in Table 1.

Example 8

The same treatment as in Example 1 was carried out except that, in a manufacturing process for obtaining the acrylate-based crosslinked fiber of Example 1, the hydrolyzing time was changed to 2.5 hours and the resulting acrylate-based crosslinked fiber was dipped in a 0.2% aqueous solution of polyethyleneimine (number-average molecular weight: 70000; amine value: 18 mmol/g) to conduct a treatment at 80° C. for 120 minutes followed by conducting washing with water and drying treatment to give a moisture-absorbing and deodorizing fiber. The result of evaluation of the fiber is shown in Table 1.

Example 9

The same treatment as in Example 4 was carried out except that polyethyleneimine was changed to polyethyleneimine having the number-average molecular weight of 300 (amine value: 21 mmol/g) to give a moisture-absorbing and deodorizing fiber. The result of evaluation of the fiber is shown in Table 1.

Example 10

The same treatment as in Example 4 was carried out except that an acrylate-based crosslinked fiber having calcium salt-form carboxyl group prepared by dipping the acrylate-based crosslinked fiber of Example 1 into a 5% aqueous calcium chloride solution followed by treating at 60° C. for 2 hours was used in place of the acrylate-based crosslinked fiber of Example 2 to give a moisture-absorbing and deodorizing fiber. The result of evaluation of the fiber is shown in Table 1.

Comparative Example 1

The same treatment as in Example 4 was carried out except that no treatment with polyethyleneimine was carried out to give a fiber of Comparative Example 1. The result of evaluation of the fiber, that is to say acrylate-based crosslinked fiber is shown in Table 1.

Comparative Example 2

The same treatment as in Example 4 was carried out except that an acrylate-based crosslinked fiber prepared by changing the hydrolyzing time to 0.5 hour in a manufacturing process for preparing the acrylate-based crosslinked fiber of Example 1 was used in place of the acrylate-based crosslinked fiber of Example 2 to give a fiber of Comparative Example 2. The result of evaluation of the fiber is shown in Table 1.

Comparative Example 3

The same treatment as in Example 4 was carried out except that the concentration of aqueous polyethyleneimine solution was changed to 0.1% to give a fiber of Comparative Example 3. The result of evaluation of the fiber is shown in Table 1.

TABLE 1

| | Amount of carboxyl group [mmol/g] | Amount of amino group [mmol/g] | Moisture-absorbing rate [%] | Smell-removing rate [%] | | | | | Molecular weight of polyethyleneimine | Salt-form/H-form ratio |
| --- | --- | --- | --- | --- | --- | --- | --- | --- | --- | --- |
| | | | | Ammonia | Acetic acid | Isovaleric acid | Nonenal | Acetaldehyde | | |
| Example 1 | 3.5 | 0.3 | 24 | 91 | 92 | 91 | 94 | 92 | 600 | 76/24 |
| Example 2 | 6.4 | 0.8 | 40 | 93 | 96 | 95 | 98 | 94 | 600 | 76/24 |
| Example 3 | 7.4 | 2.7 | 58 | 96 | 98 | 98 | 97 | 98 | 70000 | 76/24 |
| Example 4 | 6.4 | 1.1 | 46 | 99 | 99 | 93 | 98 | — | 10000 | 76/24 |
| Example 5 | 6.4 | 1.7 | 47 | 99 | 98 | 99 | 98 | — | 10000 | 76/24 |
| Example 6 | 6.4 | 2.8 | 42 | 78 | 99 | 99 | 99 | — | 1800 | 76/24 |
| Example 7 | 6.4 | 0.2 | 26 | 99 | 98 | 86 | 82 | — | 10000 | 43/57 |
| Example 8 | 7.2 | 0.2 | 59 | 99 | 96 | 90 | 83 | — | 70000 | 76/24 |
| Example 9 | 6.4 | 3.3 | 48 | 99 | 99 | 99 | 92 | — | 300 | 76/24 |
| Example 10 | 6.4 | 2.2 | 21 | 99 | 99 | 96 | 99 | — | 10000 | 76/24 |
| Comparative Example 1 | 6.4 | 0 | 47 | 99 | 96 | 66 | 7 | — | — | 76/24 |

TABLE 1-continued

| | Amount of carboxyl group [mmol/g] | Amount of amino group [mmol/g] | Moisture-absorbing rate [%] | Smell-removing rate [%] | | | | | Molecular weight of polyethyleneimine | Salt-form/H-form ratio |
|---|---|---|---|---|---|---|---|---|---|---|
| | | | | Ammonia | Acetic acid | Isovaleric acid | Nonenal | Acetaldehyde | | |
| Comparative Example 2 | 2.6 | 0.7 | 18 | 67 | 77 | 72 | 93 | — | 10000 | 76/24 |
| Comparative Example 3 | 6.4 | 0.1 | 45 | 98 | 97 | 76 | 52 | — | 10000 | 76/24 |

As will be noted from each of Examples and from Comparative Examples 1 and 3 in Table 1, deodorizing performance to acidic substance and aldehyde was greatly enhanced as a result of adhesion of a basic polymer in a specific amount onto the fiber surface. Further, neither deodorizing performance to a basic substance nor moisture-absorbing performance was significantly inhibited as a result thereof. As such, the moisture-absorbing and deodorizing fiber of the present invention exhibits high deodorizing performance to any of acid substance, aldehyde and acidic substance and also exhibits a high moisture-absorbing performance. In addition, it is also noted that, when the amount of carboxyl group is small as in Comparative Example 2, the amount of amino group or, in other words, the amount of basic polymer which can adhere to the fiber surface also lowers whereby no sufficient performance can be achieved. Incidentally, the referential symbol "—" for the smell-removing rate for acetaldehyde in the table shows that no measurement was done.

Further, the moisture-absorbing rate and the retention rate of the deodorizing performance of the moisture-absorbing and deodorizing fibers prepared in Examples 2 and 4 after washing for ten times were evaluated. The result is shown in Table 2.

TABLE 2

| | Moisture-absorbing rate [%] | Retention rate of the deodorizing performance [%] | | | |
|---|---|---|---|---|---|
| | | Ammonia | Acetic acid | Isovaleric acid | Nonenal |
| Example 2 | 39 | 99 | 97 | 98 | 100 |
| Example 4 | 44 | 100 | 100 | 94 | 96 |

It can be understood from Examples 2 and 4 in Table 1 and also from Table 2 that the moisture-absorbing and deodorizing fiber of the present invention can maintain its excellent deodorizing performance even upon repeated washings.

The invention claimed is:

1. A moisture-absorbing and deodorizing fiber, characterized in that, a basic polymer is ionically-bonded in an amount of 0.2 to 4 mmol/g as an amount of amino group onto the surface of a moisture-absorbing fiber having a crosslinked structure and also having 3 to 8 mmol/g of carboxyl group.

2. The moisture-absorbing and deodorizing fiber according to claim 1, wherein moisture-absorbing rate under the condition of 20° C. and 65% RH is 20 to 60% by weight.

3. The moisture-absorbing and deodorizing fiber according to claim 1, wherein ammonia-removing rate is 70% or more, acetic acid-removing rate is 80% or more, isovaleric acid-removing rate is 85% or more and nonenal-removing rate is 75% or more.

4. The moisture-absorbing and deodorizing fiber according to claim 1, wherein retention rate of the deodorizing performance to each of ammonia, acetic acid, isovaleric acid and nonenal after washing for ten times is 90% or more.

5. The moisture-absorbing and deodorizing fiber according to claim 1, wherein average molecular weight of the basic polymer is 300 or more.

6. A method for manufacturing the moisture-absorbing and deodorizing fiber mentioned in claim 1, characterized in that, a basic polymer is ionically-bonded to a moisture-absorbing fiber in which the ratio of salt-form carboxyl group to H-form carboxyl group is within a range of 40:60 to 100:0.

7. A moisture-absorbing and deodorizing fiber structure containing the moisture-absorbing and deodorizing fiber mentioned in claim 1.

* * * * *